United States Patent [19]

Hirashima et al.

[11] 4,393,216

[45] Jul. 12, 1983

[54] METHOD OF PRODUCING AMINOBENZIMIDAZOLONES

[75] Inventors: Tsuneaki Hirashima; Toshiyuki Miyata, both of Sakai; Yoshikazu Yamamoto, Ikeda; Mitsuyuki Kato, Neyagawa, all of Japan

[73] Assignees: Showa Chemical Co., Ltd.; Osaka Municipal Government, both of Japan

[21] Appl. No.: 275,619

[22] Filed: Jun. 22, 1981

[30] Foreign Application Priority Data

Dec. 30, 1980 [JP] Japan .............................. 55-187383

[51] Int. Cl.³ .......................................... C07D 235/26
[52] U.S. Cl. ..................................... 548/305; 564/441
[58] Field of Search ......................................... 548/305

[56] References Cited

PUBLICATIONS

Sonoda, N., et al., *J. Am. Chem. Soc.*, 93, 6344, (1971).
Kondo, K., et al., *Angew. Chem. Int. Ed. Engl.*, 18, 691, 692, (1979).
Falbe, J. (Editor), *New Syntheses with Carbon Monoxide*, Springer-Verlag, New York, 1980, pp. 291–292, 296–297, 303–307.

*Primary Examiner*—Richard A. Schwartz
*Attorney, Agent, or Firm*—Wenderoth, Lind & Ponack

[57] ABSTRACT

A method of producing aminobenzimidazolones which comprises reacting a compound I having the general formula

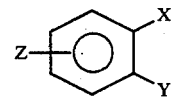

wherein X, Y and Z independently represent a substituent selected from the group consisting of a nitro group and an amino group, with carbon monoxide in solvent in the presence of selenium and an inorganic base or an organic base, and in the presence of water when the compound I has nitro groups, thereby providing a compound II having the general formula

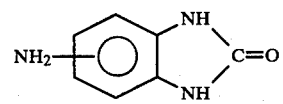

13 Claims, No Drawings

METHOD OF PRODUCING AMINOBENZIMIDAZOLONES

The present invention relates to a method of producing aminobenzimidazolones.

Aminobenzimidazolones are widely used as intermediates for producing dyestuffs, pigments, medicines and other useful chemicals, and their use is now further expanding. However, the conventional methods of producing aminobenzimidazolones have various disadvantages. For example, 5-aminobenzimidazolone has been for a long time produced by the nitration of benzimidazolone to 5-nitrobenzimidazolone followed by the reduction thereof, or by the amidation of 2,4-dinitrophenylurethane in the presence of tin and hydrochloric acid. As apparent, in the former method the overall yield is low, while in the latter method the feed material is not readily available, thus resulting in high production cost.

It is therefore an object of the present invention to provide a novel method of producing aminobenzimidazolones which is simple in operation, mild in reaction conditions and is able to provide aminobenzimidazolones of high purity in high yields.

It is another object of the invention to provide a method of producing aminobenzimidazolones using a novel catalyst which is readily recovered and reused as is.

It is still a more specific object of the invention to provide a method of producing 5-aminobenzimidazolone in a single step reaction from a readily available feed material such as 2,4-dinitroaniline.

Other objects and features of the invention will become apparent from the following description and claims attached hereto.

According to the invention, there is provided a method of producing aminobenzimidazolones which comprises reacting a compound I having the general formula

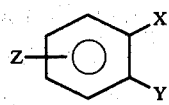

wherein X, Y and Z independently represent a substituent selected from the group consisting of a nitro group and an amino group, with carbon monoxide in solvent in the presence of selenium and an inorganic base or an organic base, and in the presence of water when the compound I has nitro groups, thereby providing a compound II having the general formula

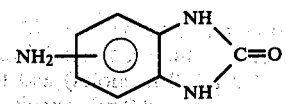

The feed compound I used in the invention has two substituents X and Y at the ortho position of X, and a third substituent Z at 4- or 5-position. The substituents X, Y and Z independently represent a nitro or an amino group. Preferred examples of the feed compound are 2,4-dinitroaniline and 3,4-diaminonitrobenzene. Other diaminonitrobenzenes, dinitroanilines, triaminobenzenes and trinitrobenzenes, for example, 2,4-diaminonitrobenzene, 2,5-diaminonitrobenzene and 1,2,4-triaminobenzene may be use as a feed material, if necessary. The feed materials as above defined provide aminobenzimidazolones in which the amino substituent is derived from the third substituent Z even if it is a nitro group since the nitro group contained in the feed material is simultaneously reduced to an amino group in the presence of water as is described later during the reaction.

The feed compound may additionally have inactive substituents. The inactive substituent herein means any substituent which will not exert a harmful influence upon the reaction of the feed compound to the corresponding aminobenzimidazolones II, and includes aliphatic, alicyclic and aromatic hydrocarbon residuals, heterocyclic residuals, alkoxy groups, aryloxy groups and halogens. For example, the inactive substituent may be methyl, ethyl, propyl, butyl, pentyl, hexyl, 2-ethylhexyl, cyclohexyl, phenyl, methoxy, propoxy, phenoxy, chlorine or bromine.

In the invention is used selenium as a starting catalyst. This means that selenium is added to the reactants in solvent at the start of the reaction, but the selenium is converted into other forms during the reaction. Selenium used in the invention is preferably in the form of powder, and commercially available selenium powder is suitably used in the invention. Although the amount of selneium used is not critical in the invention, and the more the amount of selenium used, the greater the reaction rate. Selenium may be used in the amount of 0.1 to 10 moles per mole of the feed compound I so as to facilitate the recovery of selenium after the reaction. Usually, 0.1 to 5 and preferably 0.5 to 2 moles per mole of the feed compound are used.

In the reaction according to the invention, it is likely that selenium reacts with carbon monoxide in the presence of bases to provide selenium carbonyl (SeCO), which in turn reacts with water if any in the reaction system to provide selenium hydride ($H_2Se$). The selenium hydride will form a salt with a base and is dissolved in solvent. Nitro groups, when contained in the feed material I, are reduced to amino groups by the selenium hydride, which in turn is oxidized to selenium, with the generation of water. The thus formed selenium however immediately reacts with carbon monoxide and then with water to generate selenium hydride. Accordingly, the reaction system of the invention is substantially homogeneous in almost all cases. On the other hand, selenium carbonyl inserts between the nitrogen and hydrogen atom of amino group of the feed compound I to convert the amino into —NHCOSeH group, and the carbonyl carbon of the group attacks the amino group at the ortho position of the carbonyl group in an electrophilic manner, thereby forming imidazolones by ring closure, with the formation of selenium hydride.

Therefore, when the feed compound contains nitro groups, water seems indispensable at least at the start of the reaction. Accordingly, although not critical, water is usually added to the reactants in amounts of 1 to 100 moles per mole of selenium when the feed compound has nitro groups to be reduced to amino groups.

However, it should be understood that the present invention is not confined to any theory.

In the reaction of the invention, either inorganic or organic bases are used. As inorganic bases are used, for example, carbonates, bicarbonates, hydroxides, oxides and sulfides of alkali metals and alkaline earth metals. The sulfides include mono- and polysulfides. Preferable examples of inorganic bases are potassium carbonate, sodium carbonate, potassium hydroxide, sodium hydroxide, sodium sulfides and potassium sulfides. Nitrogen-containing organic bases are more preferred, and tertiary amines and N,N-dialkylamides are the most preferred. Examples are aliphatic tertiary amines such as triethylamine, tripropylamines, tributylamines, tri-2-ethylhexylamine, heterocyclic tertiary amines such as pyridine, alkylpyridine including picolines and lutidines, N-alkylpyrrolidines including N-methylpyrrolidines and N-alkylpyrrolidones including N-methylpyrrolidone. Further examples are N,N-dimethylformamide and N,N-dimethylacetamide.

The amount of base is not critical in the invention since bases may be used as solvents as described later, but usually 1 to 10 moles per mole of the feed material when a solvent other than the base is used, preferably in the range of 2 to 5 moles per the feed material.

The solvent used in the invention is either water or organic solvents which may contain water. The organic solvent used should exert no harmful influence upon the reaction and should not be reduced in the reaction. Accordingly, preferable solvents used in the invention are ethers, amines, amides and hydrocarbons. The most preferred solvents are ethers such as diethylether, tetrahydrofuran, dioxane, tertiary amines such as triethylamine, pyridine and N-methylpyrrolidone, and N,N-dialkylamides such as N,N-dimethylformamide. As will be apparent, the bases which are beforementioned may be used as solvents in the invention. Hydrocarbons such as benzene and hexane may also be used as solvent if desired alone or in combination with other organic polar solvents such as tertiary amines and ethers as mentioned above.

Water alone may be used as solvent, but since some of the feed materials may be less soluble in water and also since the reaction rate is relatively small in water, it is desired to use water in combination with aforesaid organic polar solvents.

The reaction of the invention is carried out in an atmosphere of carbon monoxide, of which pressure is usually in the range of 1 to 100 Kg/cm$^2$, preferably 2 to 50 Kg/cm$^2$. Too a high pressure is preferably avoided so that undesired side reactions may not occur. The temperatures of reaction is not critical, but usually in the range of room temperature to 200° C., preferably 50° to 100° C. The reaction will complete usually within ten hours, and in many cases four to five hours are sufficient for the reaction of the invention.

As previously stated, the reaction system of the invention is substantially homogeneous, and as a result selenium is readily recovered according to the invention. After the reaction, air is introduced into the reaction mixture to decompose selenium compounds dissolved in the reaction mixture, thereby to precipitate black metallic selenium via red amorphous selenium. The selenium is filtered off from the reaction mixture, washed, and the thus recovered selenium can be used as catalyst as it is in the invention. The filtrate combined with the washings are distilled off preferably under reduced pressure to leave aminobenzimidazolones of high purity in high yields. The aminobenzimidazolones thus obtained are so high in purity that further purification is not necessary for almost all the purposes. When necessary, however, the product may be, for example, recrystallized from alcohol or aqueous alcohol.

According to the invention aminobenzimidazolones of high purity are formed in high yields by a single step reaction of feed compound such as dinitroanilines, for instance, 5-aminobenzimidazolone from 2,4-dinitroaniline. Furthermore, the reaction conditions are mild but also selenium is readily recovered and can be reused as is.

The invention will be understood more readily with reference to the following examples; however, these examples are intended to illustrate the invention and are not to be construed to limit the scope of the invention.

EXAMPLE 1

2,4-Dinitroaniline 2.29 g (12.5 m moles), selenium powder 0.99 g (12.5 m moles), water 1.6 ml (89 m moles), triethylamine 5.0 g (50 m moles) and tetrahydrofuran 100 ml were placed in a 200-ml capacity autoclave, and the atmosphere in the autoclave was replaced by carbon monoxide of 20 Kg/cm$^2$.

The contents in the autoclave was heated to a temperature of 80° C., and held at the temperature with stirring for five hours, cooled to room temperature, and carbon monoxide was removed from the autoclave by introducing air thereinto.

The reaction mixture was taken out of the autoclave, stirred in air for two hours to liberate metallic selenium as precipitates. The selenium was separated by filtration, washed with methanol. The filtrate combined with the washings was distilled off under reduced pressure to leave 5-aminobenzimidazolone 1.87 g (98.4% yield) of 96.3% purity.

In a second run, the pressure of carbon monoxide in the autoclave was held at 10 Kg/cm$^2$ by supplementing carbon monoxide into the autoclave as it is consumed, and the yield was 99.3 %.

EXAMPLES 2-8

5-Aminobenzimidazolone was prepared from 2,4-dinitroaniline in similar manners as in EXAMPLE 1, and the results were shown in Table.

EXAMPLE 9

3,4-Diaminonitrobenzene 1.91 g (12.5 m moles), selenium powder 0.99 g (12.5 m moles), water 1.6 ml (89 m moles), triethylamine 5.0 g (50 m moles) and tetrahydrofuran 100 ml were placed in a 200-ml capacity autoclave, and stirred at a temperature of 80° C. for three hours under carbon monoxide of 20 Kg/cm$^2$. The reaction mixture obtained was worked up in the same manner as in EXAMPLE 1, to provide 5-aminobenzimidazolone 1.80 g (90.0% yield).

EXAMPLE 10

2,4-Dinitro-6-chloroaniline 2.7 g (12.5 m moles), selenium 1.98 g (25.0 m moles), water 1.6 ml (89 m moles), triethylamine 5.0 g (50 m moles) and tetrahydrofuran 100 ml were placed in a 200-ml capacity autoclave, and stirred at a temperature of 80° C. for five hours under carbon monoxide of 20 Kg/cm$^2$. The reaction mixture obtained was worked up in the same manner as in EXAMPLE 1, to provide 4-chloro-6-aminobenzimidazolone in 84% yield.

| EXAMPLES | 2 | 3 | 4 | 5 | 6 | 7 | 8 |
|---|---|---|---|---|---|---|---|
| 2,4-Dinitroaniline (m moles) | 12.5 | 12.5 | 12.5 | 12.5 | 12.5 | 25.0 | 25.0 |

-continued

| EXAMPLES | 2 | 3 | 4 | 5 | 6 | 7 | 8 |
|---|---|---|---|---|---|---|---|
| Selenium (m moles) | 12.5 | 12.5 | 6.3 | 25.0 | 12.5 | 25.0 | 25.0 |
| Bases | TEA | DMF | TEA | TEA | KOH | Py | NMP[(1)] |
|  | 50 m mol | 100 ml | 50 m mol | 50 m mol | 20 m mol | 120 ml | 120 ml |
| Water (ml) | 102 | 1.6 | 1.6 | 1.6 | 1.6 | 3.2 | 3.2 |
| Solvents (ml) | — | — | THF 100 | THF 100 | THF 100 | — | — |
| CO-Pressure (Kg/cm$^2$) | 20 | 20 | 20 | 20 | 20 | 10 | 20 |
| Reaction temperatures (°C.) | 80 | 80 | 80 | 80 | 80 | 90 | 80 |
| Reaction times (hr) | 5 | 5 | 5 | 6 | 5 | 22 | 6 |
| Yields of 5-aminobenzimidazoline (%) | 52.6 | 57.7 | 83.0 | 98.1 | 74.5 | 86.3 | 95.5 |

[(1)] NMP = N—methylpyrrolidone

What is claimed is:

1. A method of producing 5-aminobenzimidazolones which comprises reacting a 2,4-dinitroaniline with carbon monoxide in a solvent in the presence of selenium, a base selected from the group consisting of tertiary amines, N,N-dialkylamides and inorganic bases selected from the group consisting of hydroxides, oxides, carbonates, bicarbonates and sulfides or alkali metals and alkaline earth metals, and water, said 2,4-dinitroaniline containing no additional substituents or only containing substituents which are substantially inert in the reaction.

2. The method as claimed in claim 1 wherein selenium is used in the amount of 0.1 to 10 moles per mole of compound I.

3. The method as claimed in claim 1 wherein the pressure of carbon monoxide is 1 to 100 Kg/cm$^2$.

4. The method as claimed in claim 1 wherein the organic base is a tertiary amine.

5. The method as claimed in claim 4 wherein the tertiary amine is a trialkylamine, pyridine, an alkylpyridine, an N-alkylpyrrolidone or an N-alkylpyrrolidine.

6. The method as claimed in claim 5 wherein the trialkylamine is triethylamine.

7. The method as claimed in claim 1 wherein the organic base is an N,N-dialkylamide.

8. The method as claimed in claim 7 wherein the N,N-dialkylamide is N,N-dimethylformamide or N,N-dimethylacetamide.

9. The method as claimed in claim 1 wherein the inorganic base is a hydroxide, oxide, carbonate, bicarbonate or sulfide of an alkali metal or an alkaline earth metal.

10. The method as claimed in claim 9 wherein the alkali metal is potassium or sodium.

11. The method as claimed in claim 9 wherein the hydroxide is potassium hydroxide or sodium hydroxide.

12. The method as claimed in claim 1 wherein the reactant is 2,4-dinitroaniline and the product is 5-aminobenzimidazolone.

13. the method as claimed in claim 1 wherein the reactant is 2,4-dinitro-6-chloroaniline and the product is 4-chloro-6-aminobenzimidazolone.

* * * * *